(12) United States Patent
Tsurumaki (10) Patent No.: US 11,389,324 B2
(45) Date of Patent: Jul. 19, 2022

(54) PACKAGING MEMBERS AND PACKAGE

(71) Applicant: Takahiko Tsurumaki, Gosen (JP)

(72) Inventor: Takahiko Tsurumaki, Gosen (JP)

( * ) Notice: Subject to any disclaimer, the term of this patent is extended or adjusted under 35 U.S.C. 154(b) by 0 days.

(21) Appl. No.: 16/976,962

(22) PCT Filed: Mar. 5, 2018

(86) PCT No.: PCT/JP2018/008294
§ 371 (c)(1),
(2) Date: Aug. 31, 2020

(87) PCT Pub. No.: WO2019/171421
PCT Pub. Date: Sep. 12, 2019

(65) Prior Publication Data
US 2021/0000640 A1 Jan. 7, 2021

(51) Int. Cl.
*A61F 6/04* (2006.01)
*A61F 6/00* (2006.01)
*B65D 75/30* (2006.01)
*B65D 75/52* (2006.01)

(52) U.S. Cl.
CPC ............ *A61F 6/005* (2013.01); *A61F 6/04* (2013.01); *B65D 75/30* (2013.01); *B65D 75/52* (2013.01)

(58) Field of Classification Search
CPC ........... A61F 6/005; A61F 6/04; B65D 75/30; B65D 75/52
USPC .......................................................... 206/69
See application file for complete search history.

(56) References Cited

U.S. PATENT DOCUMENTS

| | | | | |
|---|---|---|---|---|
| 3,425,539 A * | 2/1969 | Mach | ....................... | B60N 3/08 206/216 |
| 5,044,492 A * | 9/1991 | Auerbach | ............... | A61F 6/005 206/69 |
| 7,422,105 B2 * | 9/2008 | Loyd | .................. | B65D 75/5855 206/438 |
| 8,256,609 B1 * | 9/2012 | Lee | ......................... | A61F 6/005 206/69 |

(Continued)

FOREIGN PATENT DOCUMENTS

| CN | 204323918 U | 5/2015 |
|---|---|---|
| CN | 206107897 U | 4/2017 |

(Continued)

OTHER PUBLICATIONS

Notice of Reason(s) for Rejection for Japanese Patent Application No. 2020-504486 dated Jul. 13, 2021, 6 pages including English translation.

(Continued)

*Primary Examiner* — Jacob K Ackun
(74) *Attorney, Agent, or Firm* — Withrow & Terranova, P.L.L.C.; Vincent K. Gustafson (57) ABSTRACT

Packaging member includes a first film and a second film, and are configured capable of accommodating an accommodated object between the first film and the second film. The packaging member is provided with an orientation indicating portion on at least either one of the first film and the second film, which indicates an orientation of the accommodated object with reference to the packaging member. The orientation indicating portion includes a phosphorescent layer containing a phosphorescent material.

9 Claims, 6 Drawing Sheets

(56) References Cited

U.S. PATENT DOCUMENTS

| | | | | |
|---|---|---|---|---|
| 8,584,836 B2* | 11/2013 | De Waleffe | ........ | B65D 75/5838 |
| | | | | 206/69 |
| 10,029,841 B2* | 7/2018 | Gaines | ................... | B65D 79/02 |
| 2004/0256274 A1* | 12/2004 | Betsch | ................... | B65D 75/30 |
| | | | | 206/484 |
| 2005/0133387 A1* | 6/2005 | Cohen | ................ | B65D 83/0805 |
| | | | | 206/233 |
| 2006/0124494 A1* | 6/2006 | Clark, Jr. | ........... | B65D 75/5833 |
| | | | | 206/440 |
| 2006/0147129 A1* | 7/2006 | Miller | ................ | B65D 83/7575 |
| | | | | 383/205 |
| 2008/0029101 A1* | 2/2008 | Abadi | ....................... | A61F 6/04 |
| | | | | 128/844 |
| 2011/0153527 A1* | 6/2011 | Smythe | ................. | G06Q 99/00 |
| | | | | 705/500 |
| 2012/0222974 A1* | 9/2012 | De Waleffe | ............ | A61F 6/005 |
| | | | | 206/69 |
| 2014/0174961 A1* | 6/2014 | Lee | .......................... | A61F 6/04 |
| | | | | 206/69 |
| 2015/0060311 A1* | 3/2015 | Mendoza da Silva | . | A61F 6/005 |
| | | | | 206/69 |

FOREIGN PATENT DOCUMENTS

| | | |
|---|---|---|
| JP | S5647621 U | 4/1981 |
| JP | S5687015 U | 7/1981 |
| JP | S61117171 U | 7/1986 |
| JP | S63131939 U | 8/1988 |
| JP | H0360917 U | 6/1991 |
| JP | 2010168082 A | 8/2010 |
| JP | 2013510609 A | 3/2013 |

OTHER PUBLICATIONS

Office Action for Chinese Patent Application No. 201880090831.9 dated Aug. 24, 2021, 13 pages including English translation.

International Preliminary Report on Patentability for International Patent Application No. PCT/JP2018/008294, dated Sep. 17, 2020, 7 pages.

Notice of Reasons for Rejection in Japanese Patent Application No. 2020-504486 dated Apr. 6, 2021, 8 pages including English translation.

International Search Report (Form PCT/ISA/210) with English Translation for International Application No. PCT/JP2018/008294, dated May 22, 2018, 5 pages including translation.

Written Opinion (Form PCT/ISA/237) with partial English Machine Translation for International Application No. PCT/JP2018/008294, dated May 22, 2018, 7 pages including partial English machine language translation.

Decision of Refusal for Japanese Patent Application No. 2020504486, dated Dec. 21, 2021, 4 pages including English translation.

Second Office Action for Chinese Patent Application No. 201880090831. 9, dated Mar. 7, 2022, 14 pages.

* cited by examiner

PACKAGING MEMBERS AND PACKAGE

CROSS-REFERENCE TO RELATED APPLICATION(S)

This application is the U.S. national phase under 35 U.S.C. § 371 of International Application No. PCT/JP2018/008294 filed Mar. 5, 2018, wherein the entire contents of the foregoing application are hereby incorporated by reference herein.

TECHNICAL FIELD

The present disclosure relates to a packaging member for accommodating an accommodated object.

BACKGROUND ART

Conventionally, as shown in Patent Document 1, there has been proposed a package comprising a plurality of packaging members capable of accommodating an accommodated object in a sealed state. The package has a front surface and a back surface. Moreover, the package is provided with a plurality of perforations at boundaries between the plurality of packaging members to make it easy to detach one or more packaging members.

PRIOR ART DOCUMENTS

Patent Documents

Patent Document 1: Japanese Unexamined Patent Application Publication No. 2010-168082

SUMMARY OF THE INVENTION

Problems to be Solved by the Invention

When the accommodated object has front and back sides, the front and back sides of the accommodated object are sometimes indicated on the packaging member with letters and the like so that a user can recognize an orientation of the accommodated object before the user takes out the accommodated object from the packaging member. However, visual recognizability of the packaging member is poor in a dark environment and it is difficult for the user to recognize the front or back. Consequently, there is a risk that the user cannot easily recognize the front or back of the taken-out accommodated object.

It is difficult to recognize a perforation in a dark environment. If the user mistakenly tears off a portion other than the perforation, the packaging member is opened. Consequently, the accommodated object could be taken out from the packaging member without the user's intention.

In the present disclosure, it is desirable to provide a technology that reduces incorrect handling in a dark environment.

Means for Solving the Problems

The invention of the first aspect of the present disclosure is a packaging member that comprises a first film and a second film, and is configured capable of accommodating an accommodated object between the first film and the second film. The packaging member is provided with an orientation indicating portion on at least either one of the first film or the second film to indicate orientation of the accommodated object with reference to the packaging member. The orientation indicating portion includes a phosphorescent layer containing a phosphorescent material.

With this configuration, the orientation of the accommodated object with reference to the packaging member can be recognized by a user from the orientation indicating portion emitting light. Consequently, it can reduce incorrect handling by the user in a dark environment, thereby reducing a risk of improper usage of the accommodated object.

In the above-described packaging member, the orientation indicating portion may indicate the orientation with letters. Indicating the orientation with letters by the orientation indicating portion allows the user a proper recognition of the orientation of the accommodated object.

In the above-described packaging member, the orientation indicating portion may be provided on both of the first film and the second film. Such configuration can reduce overlooking by the user, of the orientation indicating portion. It also allows the user to recognize the orientation of the accommodated object even when only either one of the orientation indicating portions emits light, the other one emits weak light, or the other one does not emit light.

In the above-described packaging member, the packaging member may accommodate a condom as the accommodated object.

The invention of the second aspect of the present disclosure is a package comprising a plurality of packaging members that are capable of accommodating an accommodated object and are consecutively connected into one. The package comprises at least one separation auxiliary, and at least one position indicating portion. The at least one separation auxiliary is for allowing the users to easily detach the two packaging members and is formed between two consecutive packaging members of the plurality of packaging members. The at least one position indicating portion is provided at an outer surface of the package to indicate a position of the separation auxiliary. The at least one position indicating portion comprises a phosphorescent layer containing a phosphorescent material.

With this configuration, the position of the separation auxiliary can be recognized by a user from the indicating portion emitting light. Thus, it can reduce incorrect handling by the user when the user tries to detach one or more packaging members from the package in a dark environment, and therefore it can reduce tearing off a position other than the separation auxiliary and unintentional exposure of the accommodated object.

In the above-described package, the separation auxiliary may be a perforation.

Besides, in the above-described package, the plurality of packaging members may comprise a front side and a back side. The position indicating portion provided on the front side and the position indicating portion provided on the back side may include at least a part differing in form from one another. Such configuration allows the user to recognize the front side or the back side of the package according to the form of the position indicating portion.

In the above-described package, the plurality of packaging members may comprise the front side and the back side. The position indicating portion may be provided on only either one of the front side or the back side. Such configuration allows the user to recognize the front side or the back side of the package according to presence/absence of the position indicating portion.

In the above-described package, the position indicating portion may comprise at least any one of a line provided over the separation auxiliary, a line provided along the separation auxiliary, and an arrow. Such configuration allows the user to clearly recognize the position of the separation auxiliary from the position indicating portion.

EXPLANATION OF REFERENCE NUMERALS

1 . . . package, 2 . . . accommodated object, 10 . . . packaging member, 11 . . . accommodating portion, 12 . . . separation auxiliary, 21 . . . first film, 22 . . . second film, 24 . . . adhering region, 31 and 32 . . . orientation indicating portion, 41, 42 . . . position indicating portion, 101, 201, 301, 401, 501, 601, 701, 801 . . . package, 311 . . . orientation indicating portion, 402, 502, 602, 702, 802a to 802c . . . position indicating portion

MODE FOR CARRYING OUT THE INVENTION

Some embodiments of the present disclosure will be described hereinafter by way of example with reference to the accompanying drawings. It is to be understood that each described below is merely one form of the present disclosure, and the present disclosure is not limited to the embodiments, but may be implemented in various forms within the technical scope of the present disclosure. Since the drawings shown below are schematic drawings, they may be different in size ratio from actual objects.

1. Embodiment

[1-1. Configuration of Package]

Figure 1A:
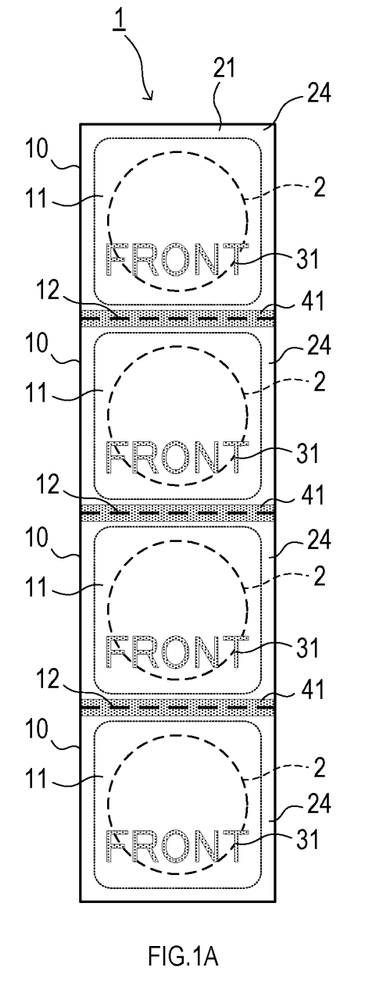
FIG. 1A is a front view of the package.
Figure 1B:
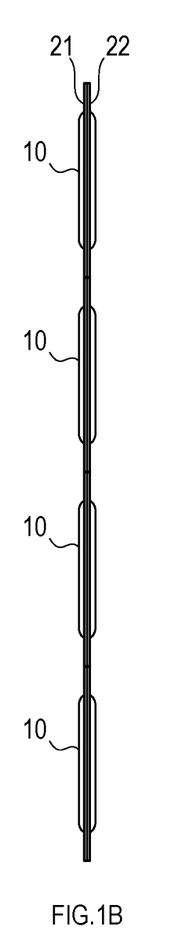
FIG. 1B is a side view of the package.
Figure 1C:
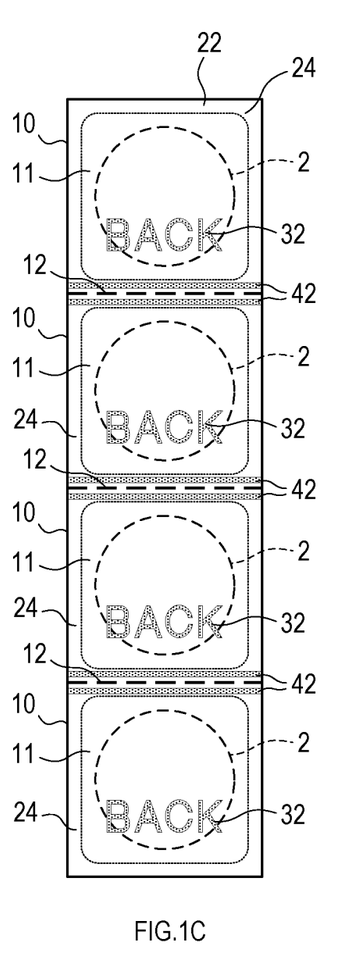
FIG. 1C is a back view of the package.

A package of an embodiment is shown in FIGS. 1A to 1C. A package 1 is formed by a plurality of packaging members 10 consecutively connected into one. In the present embodiment, the package 1 comprises four packaging members 10. The package 1 as a whole is beltlike because of the plurality of packaging members 10 connected in a row.

The plurality of packaging members 10 comprise an accommodating portion 11, which is capable of accommodating an accommodated object 2 in a sealed state. In the present embodiment, an example of accommodating a condom will be described. The accommodated object 2 is not especially limited. The packaging members 10, for example, can accommodate foods and sanitary goods. As described later, the package 1 can indicate an information with a phosphorescent layer containing a phosphorescent material, and may accommodate an object possibly used in a dark environment. Examples of the accommodated object 2 are an emergency food and a condom.

A separation auxiliary 12 is provided between two consecutive packaging members 10 of the plurality of packaging members 10 to allow the user to easily detach the two packaging members. The package 1 of the present embodiment is provided with three separation auxiliaries 12. In the present embodiment, the plurality of separation auxiliaries 12 are perforations in which intermittent cuts are formed. The plurality of separation auxiliaries 12 are formed at boundaries between the plurality of packaging members 10.

An accommodating portion 11 is formed of a first film 21 and a second film 22. In other words, the space between the first film 21 and the second film 22 is the accommodating portion 11 capable of accommodating the accommodated object 2.

The first film 21 and the second film 22 are distinguished by positionings. The first film 21 forms one side of a wall surface forming the accommodating portion 11. The second film 22 forms another side of the wall surface other than the above-described side. In each of the packaging members 10, the first film 21 and the second film 22 are adhered using adhesive or by heat fusion at an adhering region 24 having a rough-rectangular-frame shape. The accommodating portion 11 is formed of a portion surrounded by the adhering region 24 of the first film 21 and the second film 22.

The first film 21 and the second film 22 may be films having the same composition or films having different composition. The first film 21 and the second film 22 may be two different films, or the first film 21 and the second film 22 may be a single connected film. These films can be mainly formed from synthetic resin made film, metal deposited film, film with metal film, composite film formed from metal and synthetic resin and the like. These films may be films adhered with papers.

Indications or decorations by printing and the like can be provided on the surfaces of the first film 21 and the second film 22. Although an orientation indicating portion and a position indicating portion as later described are provided in the present embodiment, a decoration other than these may be provided. The first film 21 and the second film 22 themselves may be colored or transparent, or have a transmissive property.

[1-2. Orientation Indicating Portion]

A condom as the accommodated object 2 is accommodated in such a manner that it is folded in a flattened ring-like state. It is preferable that the user can recognize the orientation of the accommodated condom when taking out the condom from the accommodating portion 11.

As shown in FIGS. 1A to 1C, an outer surface of the first film 21 is provided with a plurality of orientation indicating portions 31. An outer surface of the second film 22 is provided with a plurality of orientation indicating portions 32. The plurality of orientation indicating portions 31 and the plurality of orientation indicating portions 32 indicate an orientation of the accommodated object 2 accommodated in the accommodating portion 11 with reference to the packaging member 10. In the present embodiment, the plurality of orientation indicating portions 31 are phosphorescent layers forming letters of "FRONT". Also, the plurality of orientation indicating portions 32 are phosphorescent layers forming letters of "BACK". In such a configuration, the packaging member 10 indicates the orientation of the accommodated object 2 with reference to the packaging member 10 with letters. In other words, the plurality of orientation indicating portions 31 and the plurality of orientation indicating portions 32 indicate in what orientation the accommodated object 2 is arranged inside the accommodating portion 11.

The phosphorescent layer comprises at least a phosphorescent material and a retaining material to retain the phosphorescent material.

Phosphorescent material is a material that stores light, such as visible light and UV light, and electromagnetic waves, and has a light emitting property. For example, phosphorescent materials comprising mainly strontium aluminate ($SrAl_2O_4$ or the like) with materials such as cerium, europium, neodymium, and dysprosium for changing a light emitting status added thereto may be used. However, the phosphorescent materials are not limited to these. The above-described phosphorescent material is white.

The retaining material is a material that retains the phosphorescent material, and has light transmissivity to allow the phosphorescent material to accumulate light and to emit light. Examples of the retaining materials may include gloss varnish, matt varnish, abrasion-resistive varnish, antistatic varnish, anti-blocking varnish, drying oil, paints, and adhesives.

Besides, the above-described phosphorescent layer may contain a dye or pigment. The above-described phosphorescent material is white and therefore is possibly inconspicuous to the user in a bright environment. However, by coloring the phosphorescent layer, visual recognizability of the phosphorescent layer in the bright environment is improved.

Method of forming the plurality of orientation indicating portions 31 and the plurality of orientation indicating portions 32 is not especially limited. For example, the plurality of orientation indicating portions 31 and the plurality of orientation indicating portions 32 may be formed by printing a phosphorescent layer on a film.

[1-3. Position Indicating Portion]

As shown in FIGS. 1A to 1C, the outer surface of the first film 21 is provided with a plurality of position indicating portions 41. Besides, the outer surface of the second film 22 is provided with a plurality of position indicating portions 42. The plurality of position indicating portions 41 and the plurality of position indicating portions 42 guide a position where the plurality of separation auxiliaries 12 of the package 1 are provided.

The plurality of position indicating portions 41 are belt-like each with a width, and coincide with the separation auxiliaries 12. The plurality of position indicating portions 42 are a set of two parallel lines aligned with a gap. Each of the plurality of separation auxiliaries 12 is positioned between the aforementioned two parallel lines. In this manner, the plurality of position indicating portions 41 provided on the front side of the packaging member 10 and the plurality of position indicating portions 42 provided on the back side of the packaging member 10 have different forms.

The plurality of position indicating portions 41 and the plurality of position indicating portions 42 are the above-described phosphorescent layers and may contain a dye or pigment in the same way as the plurality of orientation indicating portions 31 and the plurality of orientation indicating portions 32 do. Method of forming the plurality of position indicating portions 41 and the plurality of position indicating portions 42 is not especially limited, for example, and they can be formed by printing.

[1-4. Effects]

According to the detailed embodiment, it can reduce incorrect handling of the package 1 by the user in a dark environment. More specific effects will be described below.

(1A) The plurality of orientation indicating portions 31 and the plurality of orientation indicating portions 32 are phosphorescent layers and emit light if light or electromagnetic waves are stored therein. It allows the user to recognize the orientation of the accommodated object 2 with reference to the packaging members 10 even in a dark environment. It therefore can reduce the risk of improper usage of the accommodated object 2 caused by the user unaware of the orientation of the accommodated object 2 taken out in a dark environment.

(1B) Both of the first film 21 and the second film 22 are provided with the plurality of orientation indicating portions 31 or the plurality of orientation indicating portions 32. It can therefore reduce overlooking by the user, of the plurality of orientation indicating portions 31 and the plurality of orientation indicating portions 32. Moreover, even when only either ones of the plurality of orientation indicating portions 31 or the plurality of orientation indicating portions 32 emit light, the other ones do not emit light, or the other ones emit weak light, the user can recognize the orientation of the accommodated object 2 by checking the emitting ones.

(1C) The plurality of position indicating portions 41 and the plurality of position indicating portions 42 are phosphorescent layers and emit light if light or electromagnetic waves are stored. It therefore allows the user to recognize the position of the plurality of separation auxiliaries 12 even in a dark environment. It can reduce tearing off at a wrong position other than any of the plurality of separation auxiliaries 12 when the user tries to detach one or more packaging members 10 from the package 1 in a dark environment. Consequently, it can reduce unintentional exposure of the accommodated object 2, or losing airtightness of the accommodating portion 11.

(1D) Both of the first film 21 and the second film 22 are provided with the plurality of position indicating portions 41 or the plurality of position indicating portions 42. It can reduce overlooking by the user, of the plurality of position indicating portions 41 and the plurality of position indicating portions 42. Moreover, even when only either ones of the plurality of orientation indicating portions 41 or the plurality of orientation indicating portions 42 emit light, the other ones do not emit light, or the other ones emit weak light, the user can recognize the position of the plurality of separation auxiliaries 12 by checking the emitting ones.

2. Other Embodiments

It is to be understood that although some embodiments of the present disclosure have been described above, the present disclosure is not limited to the aforementioned embodiments, but may be implemented in various forms within technical scope of the present disclosure.

(2A) The above-described phosphorescent layer is not limited to being in composition described in the aforementioned embodiment, and adjustment such as adding other materials can be accordingly made. The plurality of orientation indicating portions 31, the plurality of orientation indicating portions 32, the plurality of position indicating portions 41, and the plurality of position indicating portions 42, as described above, may be formed not only of the phosphorescent layer but also by a combination of that and structural features of the film. For example, the orientation indicating portion and the position indicating portion may be a combination of the phosphorescent layer and an unevenness formed as a projection and/or depression on the film.

Figure 2A:
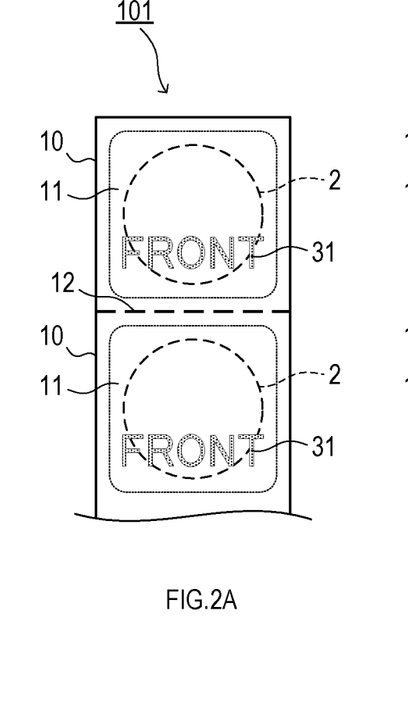
FIG. 2A is a front view of the package in a first modified example.
Figure 2B:
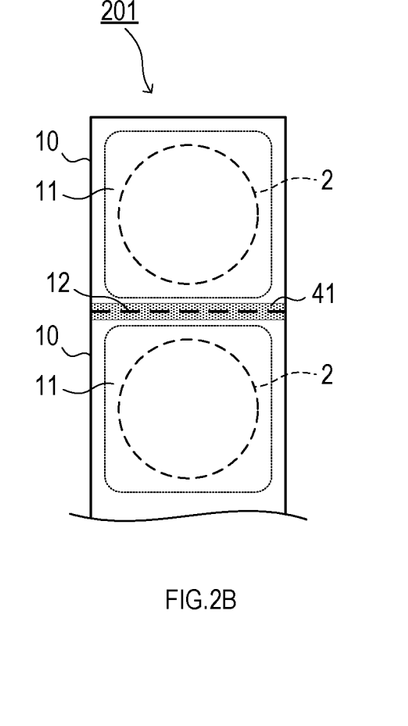
FIG. 2B is a front view of the package in a second modified example.

(2B) The aforementioned embodiment exemplified the package 1 in which both of the plurality of orientation indicating portions and the plurality of position indicating portions are provided. However, it may have a configuration in which only either ones of the one or more orientation indicating portions or the one or more position indicating portions are provided. For example, as a package 101 of the first modified example shown in FIG. 2A, the position indicating portion 41 may not be provided while the plurality of orientation indicating portions 31 are provided. Likewise, as a package 201 of the second modified example shown in FIG. 2B, the orientation indicating portion 31 may not be provided while the plurality of position indicating portions 41 are provided.

(2C) The aforementioned embodiment exemplified a configuration in which both of the first film and the second film are provided with the plurality of orientation indicating portions 31 or the plurality of orientation indicating portions 32. However, the plurality of orientation indicating portions may be provided on at least only either one of the first film or the second film.

(2D) The aforementioned embodiment exemplified a configuration in which the plurality of orientation indicating portions 31 and the plurality of orientation indicating portions 32 indicate the orientation of the accommodated object 2 with reference to the package 1 with letters. However, the orientation may be indicated in any form other than with letters as long as the orientation can be indicated.

Figure 3A:
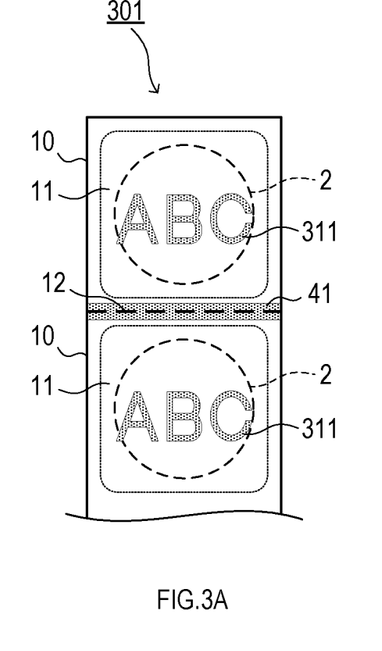
FIG. 3A is a front view of the package in a third modified example.

For example, when the front and back of the packaging member 10 and the front and back of the accommodated object 2 correspond and thus allows the user to recognize the front side of the accommodated object 2 upon recognition of the front side of the packaging member 10, the orientation indicating portion may be an indication in form such that the front side or the back side of the packaging member 10 themselves can be recognized. Specifically, as a package 301 of the third modified example shown in FIG. 3A, an orientation indicating portion 311 representing a product name, a company name or the like may be indicated on the front side surface of the packaging member 10.

Forms other than letters, for example, numbers, symbols, figures, marks, patterns and the like may be also indicated. The figures may, for example, give indications such as the position of the accommodated object 2 in the accommodating portion 11, the orientation, or a using method.

Figure 3B:
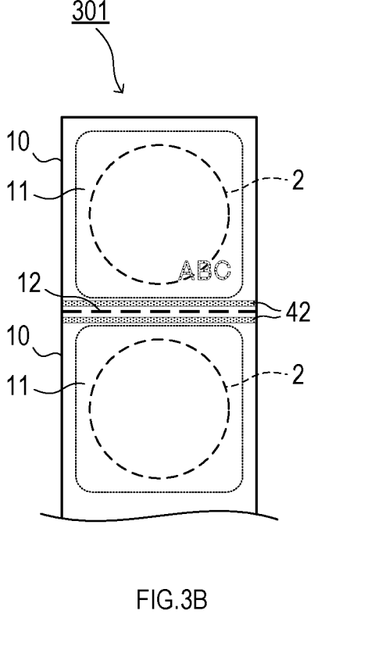
FIG. 3B is a back view of the package in the same modified example.

A surface as the back surface of the packaging member 10 is simply required to be clearly different from the front surface. For example, as shown in FIG. 3B, the same letters as the front surface may be provided in a smaller size, or no indication may be provided thereon.

(2E) Although the aforementioned embodiment exemplified a configuration in which the plurality of position indicating portions 41 or the plurality of position indicating portions 42 are provided for all of the separation auxiliaries 12, the plurality of position indicating portions 41 or the plurality of position indicating portions 42 may be provided for only some of the separation auxiliaries 12.

(2F) The aforementioned embodiment exemplified a configuration in which the plurality of position indicating portions 41 or the plurality of position indicating portions 42 are provided on both of the first film and the second film 22. However, the position indicating portions may be provided on only at least either of the first film or the second film.

The aforementioned embodiment exemplified a configuration in which the plurality of position indicating portions 41 and the plurality of position indicating portions 42 are different in form from one another. However, the plurality of position indicating portions 41 and the plurality of position indicating portions 42 may be identical in form, or may be different in some parts of the form and identical in the other parts of the form.

The plurality of position indicating portions 41 and the plurality of position indicating portions 42 being different from one another in form also allows the user to recognize the difference between the front and back of the packaging member 10.

(2G) The aforementioned embodiment exemplified a line over the plurality of separation auxiliaries 12 as the plurality of position indicating portions 41, and exemplified a combination of accommodated object two lines along the plurality of separation auxiliaries 12 as the plurality of position indicating portions 42. However, the position indicating portion may be in a form other than the above-described ones.

Figure 4A:
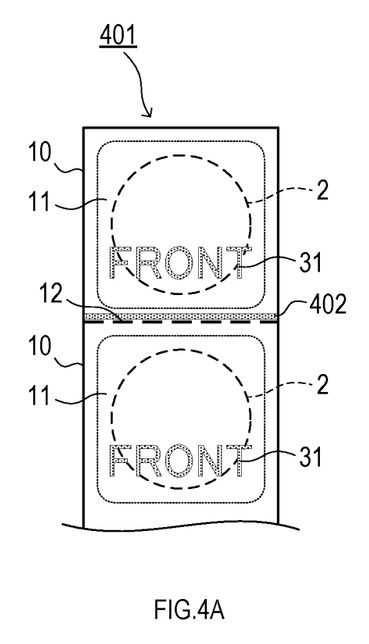
FIG. 4A is a front view of the package of a fourth modified example.
Figure 4B:
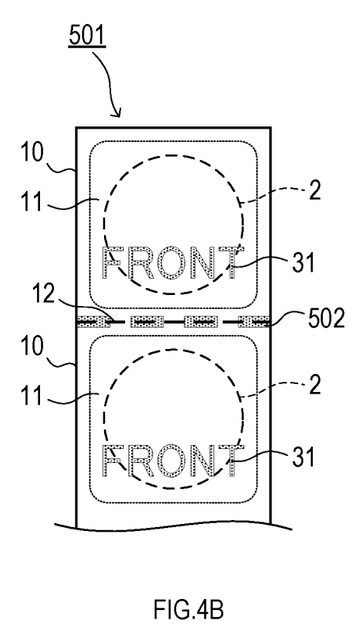
FIG. 4B is a front view of the package in a fifth modified example.

For example, as illustrated by a package 401 of the fourth modified example shown in FIG. 4A, a position indicating portion 402 may be a single line along the separation auxiliary 12. As illustrated by a package 501 of the fifth modified example shown in FIG. 4B, a position indicating portion 502 may be formed of a broken line. Although not shown, the position indicating portion may be a wavy line or zigzag line.

Figure 5A:
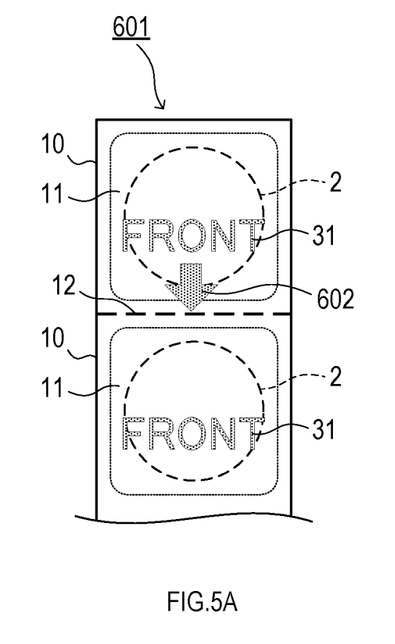
FIG. 5A is a front view of the package in a sixth modified example.
Figure 5B:
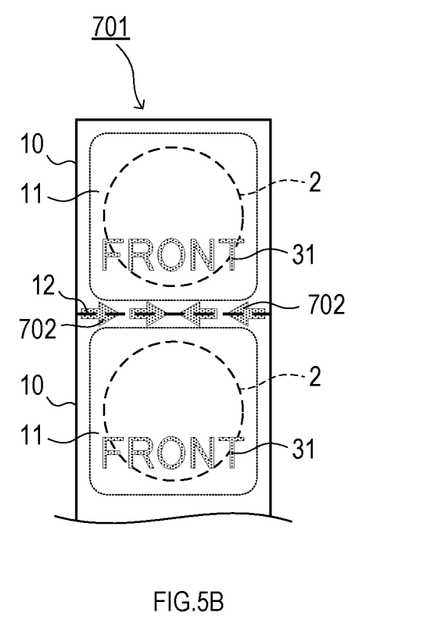
FIG. 5B is a front view of the package in a seventh modified example.

The position indicating portion may be in a form other than a line. For example, as illustrated by a package 601 of the sixth modified example shown in FIG. 5A, a position indicating portion 602 may be formed in an arrow shape of which the arrow point pointing the separation auxiliary 12. Besides, as illustrated by a package 701 of the seventh modified example shown in FIG. 5B, a plurality of position indicating portions 702 may have an arrow shape and may be arranged along a lengthwise direction of the separation auxiliaries 12.

Figure 6:
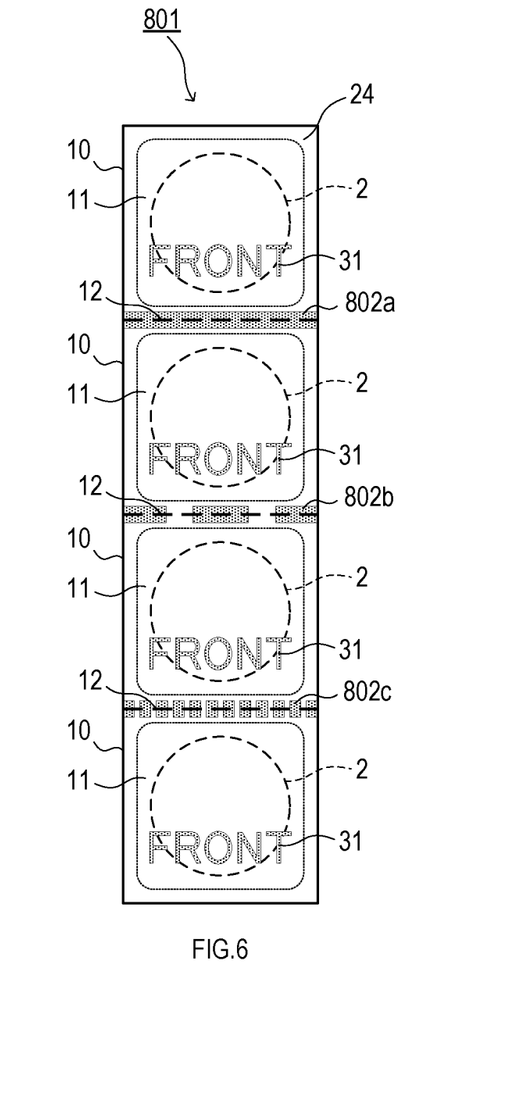
FIG. 6 is a front view of the package in an eighth modified example.

(2H) As illustrated by a package 801 of the eighth modified example shown in FIG. 6, position indicating portions 802a to 802c corresponding to each of the plurality of separation auxiliaries 12 may be different in form from one another. All of position indicating portions of the packages may be different in form from one another, or some of the position indicating portions may be identical in form.

The forms of the plurality of position indicating portions may be configured to be different from one another, whereby the position of the corresponding separation auxiliary 12 in the package, the content of the accommodated object 2, the number of packaging members 10 remaining in the packages, and the like can be recognized by the user. For example, in the package 801, the position indicating portions 802a to 802c are different in form from one another, thereby allowing the user to identify any of the plurality of separation auxiliaries 12.

(2I) The aforementioned embodiment exemplified a configuration in which the plurality of packaging members 10 are connected in a row, and the plurality of separation auxiliaries 12 are formed between each of combinations of two consecutive packaging members 10. However, a plurality of packaging members may be connected in two, three or more rows, and connected in a planarly extending manner. Besides, the number of the plurality of packaging members 10 aligned in a row is not especially limited but simply required to be two or more. In a package having a single packaging member, of course, a separation auxiliary and a position indicating portion may not be provided.

When the plurality of separation auxiliaries 12 are provided, not all of the separation auxiliaries 12 may be provided with the position indicating portions. When a single separation auxiliary 12 is provided on a package, a position indicating portion may be provided on the single separation auxiliary 12.

(2J) The aforementioned embodiment exemplified a configuration in which the separation auxiliary 12 is a perforation. However, as long as it enables the user to easily detach two consecutive packaging members, the specific configuration is not especially limited. For example, a separation auxiliary may be a part formed with the thickness thinner than the surroundings. The separation auxiliary may also be formed of materials that can be cut more easily than those materials forming the surrounding areas.

The invention claimed is:

1. A package comprising:
   a plurality of packaging members capable of accommodating an accommodated object, the plurality of packaging members being consecutively connected into one;
   at least one separation auxiliary formed between two consecutive packaging members of the plurality of packaging members, and allowing a user to easily detach the two consecutive packaging members; and
   at least one position indicating portion provided on an outer surface of the package, and indicating the position of the at least one separation auxiliary,
   wherein the at least one position indicating portion includes a phosphorescent layer containing a phosphorescent material,
   wherein each packaging member of the plurality of packaging members is formed by adhering a first film and a second film to each other at an adhering region having a frame shape that is configured to surround a periphery of an accommodated object, and
   wherein the at least one position indicating portion is arranged on the adhering region.

2. The package according to claim 1,
   wherein the at least one separation auxiliary is a perforation.

3. The package according to claim 1,
   wherein packaging members of the plurality of packaging members include front sides and back sides forming the outer surface, and
   wherein for each packaging member the at least one position indicating portion includes a first position indicating portion provided on the front side, and includes a second position indicating portion provided on the back side, with at least a part of the second positioning indicating portion differing in form from the first position indicating portion.

4. The package according to claim 1,
   wherein packaging members of the plurality of packaging members include front sides and back sides forming the outer surface, and
   wherein for each packaging member the at least one position indicating portion is provided on only one of the front side or the back side.

5. The package according to claim 1,
   wherein the at least one position indicating portion comprises at least one of a line coinciding with the at least one separation auxiliary, a line provided along the at least one separation auxiliary, and an arrow.

6. The package according to claim 1,
   wherein the frame shape comprises a substantially rectangular frame shape.

7. The package according to claim 1, wherein the adhering region is formed by heat fusion of portions of the first film and the second film.

8. The package according to claim 1, wherein the adhering region is formed by providing adhesive material between portions of the first film and the second film.

9. The package according to claim 1, wherein:
   each packaging member of the plurality of packaging members includes a front side and a back side; and
   the at least one position indicating portion is arranged on both the front side and the back side of each packaging member.

* * * * *